US009596846B2

(12) United States Patent
Goyal et al.

(10) Patent No.: US 9,596,846 B2
(45) Date of Patent: Mar. 21, 2017

(54) AGRICULTURAL PESTICIDE COMPOSITIONS

(75) Inventors: Rajesh Goyal, Bensalem, PA (US); Krish Murthy Shanmuga, Plainsboro, NJ (US)

(73) Assignee: RHODIA OPERATIONS, Paris (FR)

( * ) Notice: Subject to any disclaimer, the term of this patent is extended or adjusted under 35 U.S.C. 154(b) by 281 days.

(21) Appl. No.: 13/611,880

(22) Filed: Sep. 12, 2012

(65) Prior Publication Data

US 2013/0244878 A1 Sep. 19, 2013

Related U.S. Application Data

(60) Provisional application No. 61/573,797, filed on Sep. 12, 2011.

(51) Int. Cl.
*A01N 25/30* (2006.01)

(52) U.S. Cl.
CPC .................................... *A01N 25/30* (2013.01)

(58) Field of Classification Search
None
See application file for complete search history.

(56) References Cited

U.S. PATENT DOCUMENTS 5,874,096 A 2/1999 Hazen
6,214,771 B1 4/2001 Dexter
8,937,033 B2 * 1/2015 Alexander .................... 504/358
2002/0123430 A1 9/2002 Xu et al.
2003/0096708 A1 5/2003 Agbaje et al.
2009/0270258 A1 10/2009 Rose et al.
2010/0099569 A1 * 4/2010 Ogawa et al. ................ 504/358
2010/0113275 A1 * 5/2010 Qin et al. ...................... 504/206
2013/0150241 A1 6/2013 Elsik
2013/0244878 A1 9/2013 Goyal et al.

FOREIGN PATENT DOCUMENTS

WO 2013040006 A1 3/2013
WO 2013098220 A1 7/2013
WO 2013189773 A1 12/2013

OTHER PUBLICATIONS

Dexter, Robin W., "The Effect of Fluid Properties on the Spray Quality from a Flat Fan Nozzle," Pesticide Formulations and Application Systems: 20th Volume, ASTM STP 1400, A.K. Viets, R.S. Tann, and J.C. Mueninghoff, Eds., American Society for Testing and Materials, West Conshohocken, PA, 2001.

* cited by examiner

*Primary Examiner* — Sue Liu
*Assistant Examiner* — Thor Nielsen

(57) ABSTRACT

An aqueous pesticide compositions contain water, a pesticide, and at least one surfactant having a solubility in water of less than or equal to about 10 percent by weight, in an amount effective as a drift control agent, and a method for controlling spray drift of an aqueous pesticide composition includes the steps of incorporating in an aqueous end use pesticide composition, in an amount effective as a drift control agent, at least one surfactant having a solubility in water of less than or equal to about 10 percent by weight, and spray applying the aqueous end use pesticide composition to a target pest and/or to the environment of the target pest.

2 Claims, No Drawings

AGRICULTURAL PESTICIDE COMPOSITIONS

FIELD OF THE INVENTION

This invention relates to agricultural pesticide compositions.

BACKGROUND OF THE INVENTION

Many agricultural pesticides, including insecticides, fungicides, herbicides, miticides, and plant growth regulators, are applied in the form of a liquid composition. In addition to the pesticide, such liquid compositions typically include one or more adjuvant compounds intended to improve one or more properties of the liquid composition, such as for example, storage stability, ease of handling, and/or pesticide efficacy against target organisms.

There has been an interest in adjuvants reduce drift of spray applied pesticides and the addition of high molecular weight water soluble polymers to spray compositions as a tank mix to increase droplet size and thereby reduce drift of pesticides in known, see, for example, U.S. Pat. No. 5,874,096 and U.S. Pat. No. 6,214,771. Such polymeric drift control additives tend to perform best within a relatively narrow range of concentration, for example, in spray compositions comprising from about 0.05 to 0.15 percent by weight of such polymer. More recently other approaches, such as the use of certain "self-emulsifiable" esters as drift control agents, see U.S. Patent Publication No. 2010/0113275 A1, have been described.

There is a continuing interest in developing adjuvants for controlling drift of spray applied pesticides that exhibit high performance when present in a spray composition in low amount and that are relatively insensitive to the amount of adjuvant in the spray composition.

SUMMARY OF THE INVENTION

In a first aspect, the present invention is directed to a concentrated pesticide composition, comprising:

a liquid medium, one or more pesticide compounds, and at least one surfactant having a limited solubility in water of less than 10 percent by weight, in an amount that is effective, when the concentrated pesticide composition is diluted and spray applied, to provide improved drift control compared to an analogous diluted and spray applied pesticide composition that lacks the at least one surfactant.

In a second aspect, the present invention is directed to an aqueous end use pesticide composition, comprising:

water, one or more pesticide compounds, and at least one surfactant having a limited solubility in water of less than 10 percent by weight, in an amount effective, when the end use pesticide composition is spray applied, to provide improved drift control compared to an analogous spray applied end use pesticide composition that lacks the at least one surfactant.

In a third aspect, the present invention is directed to an aqueous surfactant composition, comprising:

water, at least 10 percent by weight of at least one surfactant having a limited solubility in water of less than 10 percent by weight, and at least one hydrotrope, in an amount effective to solubilize the at least one surfactant in the composition so that the water, surfactant, and hydrotrope form a homogeneous single phase solution at 25° C.

In a fourth aspect, the present invention is directed to a method for controlling spray drift of an aqueous end use pesticide composition that comprises one or more pesticide compounds and water, said method comprising:

incorporating in the aqueous end use pesticide composition, in an amount effective as a drift control agent, at least one surfactant having a limited solubility in water of less than 10 percent by weight in an amount that is effective, when the end use pesticide composition is spray applied, to reduce spray drift of the spray applied end use pesticide composition compared to an analogous spray applied end use pesticide composition that lacks the at least one surfactant, and spray applying the aqueous end use pesticide composition comprising the at least one surfactant to a target pest and/or to the environment of the target pest.

The at least one surfactant may be incorporated in the end use pesticide composition by for example, including the at least one surfactant as a component of a concentrated pesticide composition that is diluted to form the end use pesticide composition, by mixing the at least one surfactant with a pesticide, water, and, optionally other ingredients know in the art, to form the end use pesticide composition, or by including the at least one surfactant as a component, in combination with one or more other ingredients, of an adjuvant composition and mixing the adjuvant composition with a pesticide, water, and, optionally other ingredients know in the art, to form the end use pesticide composition.

The performance of the drift control surfactant is less sensitive to concentration than a high molecular weight polymeric drift control agent and has a less dramatic effect on the viscosity of the pesticide composition than a high molecular weight polymeric drift control agent. Compared to analogous spray compositions that lack a drift control agent, spray compositions comprising a high molecular weight drift control agent and spray compositions comprising the drift control agent surfactant each tend to exhibit fewer small droplets having a size of less than 150 μm, and compared to an analogous spray compositions comprising a high molecular weight polymeric drift control agent, spray compositions comprising the drift control agent surfactant tend to exhibit fewer large droplets having a size of greater than 500 μm, with the net result being that compared to analogous spray compositions that either lack a drift control agent or include a high molecular weight polymeric drift control agent, spray compositions comprising the drift control agent surfactant tend to exhibit relatively more droplets within the highly desirable size range of from 150-500 μm. Compared to spray application of analogous spray compositions that lack a drift control agent, spray application of spray compositions that comprise a high molecular weight polymeric drift control agent through a spray nozzle tend to exhibit a decrease in the angle of the spray exiting the spray nozzle and thus a narrower spray pattern at a given distance from the nozzle. Another advantage of the drift control agent surfactant is that compared to spray application of spray compositions that comprise a high molecular weight polymeric drift control agent, spray application of spray compositions that comprise a drift control agent surfactant tend not to exhibit as great a decrease in spray angle and therefore tend to exhibit a wider spray pattern at a given distance from the spray nozzle."

DETAILED DESCRIPTION OF INVENTION AND PREFERRED EMBODIMENTS

As used herein, the term "alkyl" means a saturated straight chain or branched chain hydrocarbon radical, such as for example, methyl, ethyl, n-propyl, iso-propyl, n-butyl, sec-butyl, t-butyl, pentyl, n-hexyl.

As used herein, the term "alkoxyl" means an oxy group substituted with an alkyl group, such as, for example, methoxyl, ethyoxyl, propoxyl.

As used herein, the term "hydroxyalkyl" means a saturated straight chain or branched chain hydrocarbon radical substituted one or more carbon atoms with a hydroxyl group, such as for example, hydroxymethy, hydroxyethyl, hydroxypropyl.

As used herein, the term "alkenyl" means an unsaturated straight chain, branched chain, or cyclic hydrocarbon radical that contains one or more carbon-carbon double bonds, such as, for example, ethenyl, 1-propenyl, and 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "aralkyl" means an alkyl group substituted with one or more aryl groups, such as, for example, phenylmethyl, phenylethyl, and triphenylmethyl.

As used herein, the term "alkylamido" means amido radical, substituted with an alkyl group, such as dodecylamido, tetradecylamido.

As used herein, the terminology "($C_m$-$C_n$)" in reference to an organic group, wherein m and n are each integers, indicates that the group may contain from m carbon atoms to n carbon atoms per group.

As used herein, the term "agronomically acceptable salts" refers to salts prepared from agronomically acceptable non-toxic bases or acids including inorganic or organic bases and inorganic or organic acids. Typical agronomically acceptable salts the compound referred to herein comprise an anion derived from the compound, for example, by deprotonation of a hydroxy or hydroxyalkyl substituent, and one or more positively charged counterions. Suitable positively charged counterions include inorganic cations and organic cations, such as for example, sodium cations, potassium cations, calcium cations, magnesium cations, isopropylamine cations, ammonium cations, and tetraalkylammonium cations.

As used herein, the terminology "end use pesticide composition" means a pesticide composition that contains pesticide in amount effective to control a target pest, such as, for example, a target plant, fungus, bacterium, or insect, when the pesticide composition is applied, typically in the form of a spray, to the pest and/or to the environment of the pest at a given application rate and the terminology "pesticide concentrate composition" means a composition that contains a relatively high concentration of pesticide that is suitable to be diluted with water to form a pesticide spray composition.

As used herein, the terminology "effective amount" in reference to the relative amount of a pesticide in a pesticide composition means the relative amount of pesticide that is effective to control a target pest, for example, a target plant, fungus, bacterium, or insect, when the pesticide composition is applied to the pest and/or to the environment of the pest at a given application rate and the terminology "herbicidally effective amount" in reference to the relative amount of herbicide in an herbicidal composition means the relative amount that is effective to control growth of a target plant when the herbicidal composition is spray applied to the target plant and/or to the environment of the plant at a given application rate.

As used herein, the term "drift" refers to off-target movement of droplets of a pesticide composition that is applied to a target pest or environment for the pest. Spray applied compositions typically exhibit decreasing tendency to drift with decreasing relative amount, typically expressed as a volume percentage of total spray applied droplet volume, of small size spray droplets, that is, spray droplets having a droplet size below a given value, typically, a droplet size of less than 150 micrometers ("μm"). Spray drift of pesticides can have undesirable consequences, such as for example, unintended contact of phytotoxic pesticides with non-pest pest plants, such as crops or ornamental plants, with damage to such non-pest plants.

As used herein, the terminology "an amount effective as a drift control agent" in reference to the drift control surfactant component of the present invention means an amount of such surfactant that, when added to a given aqueous pesticide composition and the combined aqueous pesticide composition and drift control surfactant is spray applied, is effective to reduce spray drift of the spray applied composition. Typically, the ability of a given amount of a drift control surfactant to reduce spray drift of a spray applied composition is evaluated by spray applying, under the same spray conditions, a pesticide composition that contains the given amount of the drift control surfactant and an analogous pesticide composition that lacks the drift control surfactant and then comparing the relative amount of small size spray droplets exhibited by spray applied compositions, with a reduction in the amount of small size spray droplets being indicative of the ability to reduce spray drift of the spray applied composition.

As used herein, the term "surfactant" means an amphiphilic compound that comprises a hydrophilic moiety and a hydrophobic moiety and that, when present in water, lowers the surface tension of the water and the terminology "surfactant drift control agent" means a surfactant that having limited solubility, typically solubility in water of less than 10 percent by weight.

As used herein, "liquid medium" means a medium that is in the liquid phase at a temperature of 25° C. and a pressure of one atmosphere. The liquid medium may be a non-aqueous liquid medium or an aqueous liquid medium.

In one embodiment, the liquid medium is a non-aqueous liquid medium. As used herein, the terminology "non-aqueous medium" means a single phase liquid medium that contains no more than trace amounts of water, typically, based on 100 parts by weight ("pbw") of the non-aqueous medium, no more than 0.1 pbw water. Suitable non-aqueous liquid media include organic liquids, including non-polar organic liquids, such as hexanes, cyclohexane, benzene, toluene, chloroform, diethyl ether, hydrocarbon oils, polar aprotic organic liquids, such as dichloromethane, ethyl acetate, acetone, tetrahydrofuran, and polar protic organic liquids, such as methanol, ethanol, propanol, glycerol, ethylene glycol, propylene glycol, diethylene glycol, poly(ethylene glycol)s, ethylene glycol monobutyl ether, dipropylene glycol methyl ether, and ethylene glycol phenyl ether, as well as mixtures of such liquids. In one embodiment, the non-aqueous medium comprises an organic liquid that is not miscible in all proportions with water (a "water immiscible organic liquid").

In one embodiment, the liquid medium is an aqueous liquid medium. As used herein, the terminology "aqueous medium" means a single phase liquid medium that contains more than a trace amount of water, typically, based on 100 pbw of the aqueous medium, more than 0.1 pbw water. Suitable aqueous media more typically comprise, based on 100 pbw of the aqueous medium, greater than about 5 pbw water, even more typically greater than 10 pbw water. In one embodiment, the aqueous emulsion comprises, based on 100 pbw of the aqueous medium, greater than 40 pbw water, more typically, greater than 50 pbw water. The aqueous medium may, optionally, further comprise water soluble or water miscible components dissolved in the aqueous medium. The terminology "water miscible" as used herein means miscible in all proportions with water. Suitable water miscible organic liquids include, for example, ($C_1$-$C_6$)alcohols, such as methanol, ethanol, propanol, and ($C_1$-$C_6$) polyols, such as glycerol, ethylene glycol, propylene glycol, and diethylene glycol, The composition of the present invention may, optionally, further comprise one or more water insoluble or water immiscible components, such as a water immiscible organic liquid, wherein the combined aqueous medium and water insoluble or water immiscible components form a micro emulsion, or a multi-phase system such as, for example, an emulsion, a suspension or a suspo-emulsion, in which the aqueous medium is in the form of a discontinuous phase dispersed in a continuous phase of the water insoluble or water immiscible component, or, more typically, the water insoluble or water immiscible component is in the form of a discontinuous phase dispersed in a continuous phase of the aqueous medium.

Surfactants suitable as the surfactant drift control agent of the present invention are those anionic surfactants, cationic surfactants, amphoteric/zwitterionic surfactants, non-ionic surfactants, and mixtures thereof that have limited solubility in a given liquid medium selected from water and aqueous pesticide compositions, more typically a solubility of less than 10 percent by weight (wt %) or less than 5 wt %, or less than 2 wt %, or less than 1 wt %, or less than 0.5 wt %, or less than 0.1 wt % in the liquid medium such surfactants are generally referred to herein as "surfactants having limited solubility"). As referred to herein the terminology "having a solubility of less than x wt %", where x is a number, in reference to a surfactant in a given liquid medium means that a mixture of x wt % by weight of the surfactant compound and the liquid medium at 25° C. forms two macroscopic phases or forms a single turbid macroscopic phase, typically having a turbidity greater than or equal to 10 nephelometric turbidity units ("NTU"), or greater than or equal to 5 NTU, or greater than or equal to 1 NTU, or greater than or equal to 0 NTU, as determined by using a nephelometer, such as for example, a 2100P Turbidimeter (VWR).

In one embodiment, the amount of surfactant effective as a drift control agent in a given pesticide spray composition is an amount that is greater than the solubility limit of that surfactant in that pesticide spray composition. As referred to herein, the terminology "having a solubility limit of greater than y wt %" where y is a number, in reference to a surfactant in a given pesticide composition means that a mixture of less than or equal to y wt % of the surfactant compound the pesticide composition forms a macroscopically single phase, non-turbid mixture and a mixture of greater than y wt % of the surfactant compound the pesticide composition forms two macroscopic phases or forms a single macroscopic phase having a turbidity greater than or equal to 10 NTU, or greater than or equal to 5 NTU, or greater than or equal to 1 NTU, or greater than or equal to 0 NTU, as determined by using a nephelometer.

In one embodiment, the surfactants suitable as the surfactant drift control agent of the present invention are those anionic surfactants, cationic surfactants, amphoteric/zwitterionic surfactants, non-ionic surfactants, and mixtures thereof that have a limited solubility in water and in a given pesticide composition.

In one embodiment, the surfactants suitable as the surfactant drift control agent of the present invention are those anionic surfactants, cationic surfactants, amphoteric/zwitterionic surfactants, non-ionic surfactants that are not esters, and non-ionic ester surfactants selected from fatty acid polyalkylene oxide ester surfactants, sorbitan esters, sorbitol esters, alkoxylated sorbitan esters, and alkoxylated sorbitol esters, as well as, and mixtures thereof that have a limited solubility in water.

In one embodiment, the surfactants suitable as the surfactant drift control agent of the present invention are those anionic surfactants, cationic surfactants, amphoteric/zwitterionic surfactants, non-ionic surfactants that are not esters, and non-ionic ester surfactants selected from fatty acid polyalkylene oxide ester surfactants, sorbitan esters, sorbitol esters, alkoxylated sorbitan esters, and alkoxylated sorbitol esters, as well as mixtures thereof, that have a limited solubility in a given pesticide composition.

In one embodiment, the surfactant drift control agent comprises at least one anionic surfactant. Suitable anionic surfactants having limited solubility include generally know compounds selected from, for example:

alkyl (ether) sulfate surfactants, such as sodium ($C_{18}$-$C_{20}$) alkyl sulfates, ammonium ($C_{18}$-$C_{20}$)alkyl ether sulfates, alkyl (ether) sulfonate surfactants and alkaryl (ether) sulfonate surfactants such as sodium ($C_{18}$-$C_{22}$) alpha olefin sulfonates, sodium ($C_{18}$) benzene sulfonate, monoalkyl (ether) phosphate surfactants, and dialkyl (ether) phosphate surfactants such as trialkylphosphates, alkyl (ether) carboxylate surfactants, such as sodium ($C_{18}$-$C_{22}$)alkyl carboxylates, and alkyl (ether) sulfosuccinate surfactants, such as disodium ($C_{18}$-$C_{22}$)alkyl sulfosuccinates and disodium ($C_{18}$-$C_{22}$) alkyl sulfosuccinates.

In one embodiment, the surfactant drift control agent comprises at least one cationic surfactant. Suitable cationic surfactants having limited solubility include generally know compounds selected from, for example:

quaternary amine surfactants, such as cetylpyridinium bromide, behentrimonium bromide, ethoxylated fatty amine surfactants, such as fatty amines, and tallow alkylamines with low degree of ethoxylation, and fatty imidazoline surfactants, such as isostearyl benzylimidonium chloride.

In one embodiment, the surfactant drift control agent comprises at least one amphoteric/zwitterionic surfactant. Suitable amphoteric/zwitterionic surfactants having limited solubility include generally know compounds selected from, for example:

amphoacetate surfactants, such as sodium ($C_{18}$)alkyl amphoacetate aminopropionates, such as sodium ($C_{22}$)alkyl amphopropinate, amphopropionate surfactants, such as sodium ($C_{22}$)alkyl amphopropionate, amphosulfonate surfactants, sultaine surfactants, such as alkylamidopropylhydroxy sultaines, and betaine surfactants, and sulfobetaine surfactants.

In one embodiment, the surfactant drift control agent comprises one or more nonionic ester surfactants having limited solubility selected from:

fatty acid polyalkylene oxide ester surfactants derived by alkoxylation of fatty acids, fatty acid triglycerides, or mixtures thereof, and esterification of the alkoxylated product thereof with a fatty acid or a mixture thereof, including, for example, carboxylic acid esters of alkoxylated vegetable oils, such as the oleic acid ester of ethoxylated castor oil, sorbitan esters and sorbitol esters, more typically sorbitan alkyl esters, which are, typically referred to as "Span" surfactants, and include, for example, sorbitan monolaurate (Span 20), sorbitan monopalmitate (Span 40), sorbitan tristearate (Span 65), sorbitan monooleate (Span 80), and alkoxylated sorbitan esters andalkoxylated sorbitol esters, more typically alkoxylated sorbitan alkyl esters, which are typically referred to as "tween" or "polysorbate" surfactants such as, for example, polyoxyethylene (20) sorbitan monolaurate (Tween 20 or Polysorbate 20), polyoxyethylene (20) sorbitan monopalmitate (Tween 40 or Polysorbate 40) polyoxyethylene (20) sorbitan monostearate (Tween 60 or Polysorbate 60), polyoxyethylene (20) sorbitan monooleate (Tween 80 or Polysorbate 80), and polyoxyethylene (20) sorbitan trioleate (Tween 85 or Polysorbate 85).

In one embodiment, the nonionic surfactant drift control agent is not a self-emulsifiable ester, more typically, the nonionic surfactant drift control agent is not an ester. Suitable nonionic surfactants that are not esters and that have limited solubility i include generally known compounds selected from, for example:

alkoxylated alcohols, such as decyl alcohol ethoxylates, lauryl alcohol ethoxylates, tridecyl alcohol ethoxylates, myristyl alcohol ethoxylates, cetyl alcohol ethoxylates, stearyl alcohol ethoxylates, oleyl alcohol ethoxylates, linoleyl alcohol ethoxylates and linolenyl alcohol ethoxylates, and poly(oxyethylene-oxypropylene) alcohol surfactants, such as ethoxylated and propoxylated ($C_8$-$C_{10}$)alcohols, ethoxylated and propoxylated isodecyl alcohols, alkoxylated glycol alkyl ether surfactants and alkoxylated glycol alkaryl ether surfactants, such as octaethylene glycol monodecyl ether, pentaethylene glycol monodecyl ether, each alkoxylated with from 2 to 50 oxyalkylene units per molecule. polyoxyethylene glycol ocylphenols, polyoxyethylene glycol nonylphenols, glycol stearate, glycol distearate, PEG-8 dioleate, and poly(ethylene glycol) castor oils, glycoside surfactants for example, ($C_4$-$C_{22}$)alkylhexosides, such as butylglucoside, nonylglucoside, decylglucoside, dodecylglucoside, hexadecylglucoside, octadecylglucoside, ($C_4$-$C_{22}$)alkylpolyhexosides, such as butylpolyglucosides, nonylpolyglucosides, decylpolyglucosides, tetradecylpolyglucosides, hexadecylpolyglucosides, erucylpolyglucosides, ($C_4$-$C_{22}$)alkylpentosides, such as nonylarabinosides, decylarabinoside, hexadecylarabinoside, octylxyloside, nonylxyloside, decylxyloside, hexadecylxyloside, erucylxyloside, and ($C_4$-$C_{22}$)alkylpolypentosides, such as butylpolyarabinosides, nonylpolyarabinosides, decylpolyarabinosides, hexadecylpolyarabinosides, octadecylpolyarabinosides, erucylpolyarabinosides, butylpolyxylosides, nonylpolyxylosides, decylpolyxylosides, octadecylpolyxylosides, and erucylpolyxylosides butylpoly(arabino-co-xylo)sides, nonylpoly(arabino-co-xylo)sides, decylpoly (arabino-co-xylo)sides, hexadecylpoly(arabino-co-xylo) sides, octadecylpoly(arabino-co-xylo)sides, erucylpoly (arabino-co-xylo)sides, and mixtures of any of such compounds, wherein the terminology "poly(arbino-co-xylo) side" denotes a copolymeric chain of monomeric residues of arabinose and xylose.

alkoxylated phenol surfactants, alkoxylated alkyl phenol surfactants and alkoxylated alkylaryl phenol surfactants, such as for example, octyl phenol alkoxylates, nonyl phenol alkoxylates, such as octyl phenol ethoxylates, ethoxylated nonyl phenols, lauryl phenol alkoxylates, and tristyrylphenol alkoxylates, such as ethoxylated tristyrylphenols, each alkoxylated with from 2 to 50 oxyalkylene, typically oxyethylene, oxypropylene, or a mixture thereof units per molecule, alkanolamide surfactants, such as, for example, cocamide DEA, cocamide MEA, cocamide MIPA, PEG-5 cocamide MEA, lauramide DEA, amine oxide surfactants, such as, for example, stearamine oxide, stearamidopropylamine oxide, poly(oxyethylene-oxypropylene) block copolymer surfactants, typically referred to as "Poloxamers", such as, for example, Poloxamer 181.

chlorine capped ethoxylates, and mercaptan ethoxylates.

In one embodiment, the surfactant drift control agent comprises one or more alkoxylated alcohols selected from alkoxylates, more typically ethoxylates, of linear or branched, saturated or unsaturated ($C_{10}$-$C_{18}$)alkanols, such as, for example, decyl alcohol ethoxylates, lauryl alcohol ethoxylates, tridecyl alcohol ethoxylates, myristyl alcohol ethoxylates, cetyl alcohol ethoxylates, stearyl alcohol ethoxylates, oleyl alcohol ethoxylates, linoleyl alcohol ethoxylates and linolenyl alcohol ethoxylates, and mixtures thereof. Suitable alkoxylated alcohols may be alkoxylated with from 1 to 30, more typically with from 1 to 20 moles of alkylene oxide per mole of alcohol. In one embodiment, the surfactant drift control agent comprises an alkoxylated alcohol selected from alkoxylated alcohols, having an HLB of less than or equal to 15, more typically less than or equal to 12. In one embodiment, the surfactant drift control agent comprises an alkoxylated alcohol selected from ethoxylated oleyl alcohols having an HLB of less than 9.

In one embodiment, the surfactant drift control agent comprises one or more fatty acid polyalkylene oxide ester surfactants, wherein such fatty acid polyalkylene oxidel ester surfactants comprise a product derived by alkoxylation, more typically by ethoxylation, of fatty acids, fatty acid triglycerides, or mixtures thereof, more typically, of saturated or unsaturated ($C_8$-$C_{22}$) fatty acids, which may optionally be substituted on one or more carbon atoms with hydroxyl groups, triglycerides of such fatty acids, or a mixture thereof, typically with from 1 to 30, more typically with from 5 to 20 moles of alkylene oxide per mole of fatty acid or fatty acid triglycerides and esterification of the alkoxylated product thereof with a fatty acid or a mixture of fatty acids, more typically ($C_8$-$C_{22}$) fatty acids, including, for example, the oleic acid ester of ethoxylated castor oil.

In one embodiment, the surfactant drift control agent comprises one or more sorbitan esters or sorbitol esters having an HLB of less than or equal to 15, more typically less than or equal to 12. In one embodiment, the surfactant drift control agent comprises one or more sorbitan esters selected from sorbitan monolaurate (Span 20), sorbitan monopalmitate (Span 40), sorbitan tristearate (Span 65), and sorbitan monooleate (Span 80).

In one embodiment, the surfactant drift control agent comprises one or more alkoxylated sorbitan esters or alkoxylated sorbitol esters having an HLB of less than or equal to 15, more typically less than or equal to 12. In one embodiment, the surfactant drift control agent comprises one or more alkoxylated sorbitan esters selected from polyoxyethylene (20) sorbitan monolaurate (Tween 20 or Polysorbate 20), polyoxyethylene (20) sorbitan monopalmitate (Tween 40 or Polysorbate 40) polyoxyethylene (20) sorbitan monostearate (Tween 60 or Polysorbate 60), and polyoxyethylene (20) sorbitan monooleate (Tween 80 or Polysorbate 80), and polyoxyethylene (20) sorbitan trioleate (Tween 85 or Polysorbate 85).

In one embodiment, the pesticide concentrate composition according to the present invention comprises, based on 100 parts by weight of the pesticide concentrate composition:

from about 9.5 to about 97.5 pbw, more typically from about 20 to about 83 pbw, water, from about 2 pbw to about 90, more typically from about 15 pbw to about 65 pbw, of one or more pesticide compounds, and from about 0.5 to about 30 pbw, more typically from about 2 to about 20 pbw, of at least surfactant having limited solubility, typically solubility in water of less than 10 percent by weight.

The pesticide concentrate and end use pesticide compositions of the present invention may optionally further comprise one or more other surfactants, in addition to the surfactant having limited solubility, wherein such other surfactants each have a higher solubility, for example, a solubility of greater than 10 wt %, in water than the surfactant having limited solubility, as determined by the above described method for determining solubility and are selected from anionic surfactants, cationic surfactants, amphoteric/zwitterionic surfactants, nonionic surfactants, and mixtures thereof.

Suitable pesticides are biologically active compounds used to control agricultural pests and include, for example, herbicides, plant growth regulators, crop dessicants, fungicides, bacteriocides, bacteriostats, insecticides, and insect repellants, as well as their water soluble salts and esters. Suitable pesticides include, for example, triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; isoxazolidone herbicides, phenoxyacetic acids; diphenyl ether herbicides such as fluazifop, acifluorfen, bifenox, or oxyfluorfen; dinitro aniline herbicides such as trifluralin; organophosphonate herbicides such as glufosinate salts and esters and glyphosate salts and esters; dihalobenzonitrile herbicides such as bromoxynil, or ioxynil, benzoic acid herbicides, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chloronated aromatic fungicides such as chloroneb; dichloro aniline fungicides such as iprodione, strobilurin fungicides such as kresoxim-methyl, trifloxystrobin or azoxystrobin; chlorothalonil; copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources.

In one embodiment, the pesticide comprises one or more compounds selected from herbicides, plant growth regulators, crop dessicants, fungicides, bacteriocides, bacteriostats, insecticides, miticides, nematocides, insect repellants, and mixtures thereof.

In one embodiment, the pesticide is an herbicide and the pesticide composition is an herbicide composition.

In one embodiment, the pesticide comprises one or more herbicide compounds selected from glyphosate, glufosinate, their respective water soluble salts and esters, and mixtures thereof.

In one embodiment, the herbicide composition comprises one or more herbicide compounds selected from glyphosate, water soluble glyphosate salts, water soluble glyphosate esters, and mixtures thereof, more typically selected from the sodium salt of glyphosate, the potassium salt of glyphosate, the ammonium salt of glyphosate, the dimethylamine salt of glyphosate, the isopropyl amine salt of glyphosate, the trimesyl salt of glyphosate, and mixtures thereof.

In one embodiment, the concentrated pesticide composition of the present invention comprises, based on 100 pbw of the pesticide composition, from about 2 pbw, more typically from about 15 pbw, to about 90 pbw, more typically about 65 pbw, of the one or more pesticide compounds.

Suitable aqueous diluents comprise water and may optionally further comprise one or more water miscible organic liquids, such as, for example, alcohols, for example, methanol, ethanol, or propanol, glycols, for example, ethylene glycol, propylene glycol, or butylene glycol, and/or alkylether diols for example, ethylene glycol monoethyl ether, propylene glycol monoethyl ether and diethylene glycol monomethyl ether. Most typically, the aqueous diluent is water.

In one embodiment, the present invention is directed to a method for controlling spray drift of a spray applied aqueous pesticide composition, comprising:

(a) diluting the concentrated pesticide composition of the present invention with an aqueous diluent to form an end use pesticide composition that comprises the at least one surfactant in an amount that is effective, when the end use pesticide composition is spray applied, to reduce spray drift of the spray applied end use pesticide composition compared to an analogous spray applied pesticide composition that lacks the at least one surfactant, and (b) spray applying the end use pesticide composition to the target pest and/or to the environment of the target pest.

In one embodiment, the concentrated pesticide composition of the present invention does not comprise more than 0.5 pbw per 100 pbw of the composition, more typically does not comprise more than 0.05 pbw per 100 pbw of the composition, of any oil, such as a vegetable oil, an alkylated vegetable oil, or a mineral oil, and even more typically does not comprise any oil.

In one embodiment, the concentrated pesticide composition of the present invention does not comprise more than 0.5 pbw per 100 pbw of the composition not comprise more than 0.05 pbw per 100 pbw of the composition, of any polymeric drift control agent, such as a polysaccharide drift control agent, and even more typically does not comprise any polymeric drift control agent.

In one embodiment, the concentrated pesticide composition of the present invention comprises the surfactant drift control agent as the sole drift control agent of the composition.

In one embodiment, the pesticide composition of the present invention is a pesticide concentrate composition and is diluted with water, typically in a ratio of from 1:10 to 1:100 pbw pesticide concentrate composition: pbw water to form a pesticide spray composition for applying to target pests.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example, 0-0-1 3%-S; 3%-Zn; 2%-Fe; 2%-Mn and mixtures thereof. In one embodiment, the pesticide composition comprises from about 85 to about 99 pbw, more typically from about 90 to about 99 pbw, and even more typically from about 93 to about 99 pbw, of a mixture of fertilizer and water.

In one embodiment, the concentrated pesticide composition and/or end use pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid or other ingredients, such as for example, one or more thickeners, such as polysaccharide thickeners, and polyacrylamide thickeners, as well as antifoams, spreaders, and drift control agents.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

In one embodiment, the concentrated pesticide composition and end use pesticide composition may each further comprise one or more hydrotropes. As used herein the term "hydrotrope" means an amphiphilic compound that does not form micelles below 0.5 wt % in aqueous solutions the presence of which in an aqueous solution tends to solubilize hydrophobic compounds in the aqueous solution, and includes, for example, salts of aromatic carboxylic acids, alkaryl sulfonate salts, such as sodium xylene sulfonate and sodium toluene sulfonate, as well as alkyl phosphate esters, alkyaryl phosphate esters, phosphate polyether esters, and salts thereof, such as potassium laureth phosphate, phenol ethoxy phosphate, and alkylene glycols and polyalkylene glycols, such as propylene glycols, and polyethylene glycols. The addition of a hydrotrope to the composition of the present invention typically increases the solubility of the drift control agent surfactant in the aqueous medium and thus provide an opportunity to selectively adjust such solubility.

In one embodiment, the surfactant composition according to the present invention comprises, based on 100 parts by weight of the composition:

from about 19.9 to about 94.9 pbw, more typically from about 20 to about 79 pbw, of water, from about 0.1 to about 50 pbw, more typically from about 1 to about 20 pbw, of at least one surfactant having limited solubility, typically solubility in water of less than 10 percent by weight, and from about 5 to about 80 pbw, more typically from about 20 to about 60 pbw, of one of more hydrotropes.

As an alternative to the above described pesticide concentrate embodiment of the present invention, the at least one surfactant having limited solubility may be incorporated in the end use pesticide composition of the present invention by mixing the surfactant composition of the present invention with a separately added pesticide and water.

In one embodiment, the concentrated pesticide composition of the present invention is a concentrated herbicide composition that, when diluted and applied to the target plant and/or the environment of the target plant in a herbicidally effective amount is effective to control one or more target plant species of one or more of the following genera: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*, including annual broadleaf species such as, for example, velvetleaf (*Abutilon theophrasti*), pigweed (*Amaranthus* spp.), buttonweed (*Borreria* spp.), oilseed rape, canola, indian mustard, etc. (*Brassica* spp.), *commelina* (*Commelina* spp.), filaree (*Erodium* spp.), sunflower (*Helianthus* spp.), morning glory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), *sida* (*Sida* spp.), wild mustard (*Sinapis arvensis*) and cocklebur (*Xanthium* spp.), annual narrowleaf species such as for example, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*), perennial broadleaf species such as, for example, mugwort (*Artemisia* spp.), milkweed (*Asclepias* spp.), canada thistle (*Cirsium arvense*), field bindweed (*Convolvulus arvensis*) and kudzu (*Pueraria* spp.), perennial narrowleaf species such as for example, *brachiaria* (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.), and other perennial species such as, for example, horsetail (*Equisetum* spp.), bracken (*Pteridium aquilinum*), blackberry (*Rubus* spp.) and gorse (*Ulex europaeus*).

In one embodiment, the pesticide composition of the present invention is applied to foliage of a target plant at a rate of from about 0.25 pint, more typically about 0.5 pint, to about 5 pints, even more typically from about 1 pint to about 4 pints, as expressed in terms of the above described pesticide concentrate composition embodiment of the pesticide composition of the present invention (that is, comprising, based on 100 pbw of such composition, from about 2 to about 90 pbw) per acre.

In one embodiment, the pesticide composition is spray applied via conventional spray apparatus to foliage of one or more target plants present on an area of ground at a rate of from about 1 gallon to about 20 gallons, more typically about 3 gallons to 20 gallons, of the above described pesticide spray composition per acre of ground.

In one embodiment, the end use pesticide composition of the present invention comprises, based on 100 pbw of the end use pesticide composition, from greater than 0 to about 10 pbw, more typically from about 0.01 pbw to about 5 pbw of the one or more pesticide compounds, from greater than 0, more typically from about 0.01 pbw, even more typically from about 0.05 pbw, and still more typically from about 0.1 pbw of the drift control surfactant to about 10 pbw, more typically to about 2 pbw, even more typically to about 0.5 pbw of the surfactant having limited solubility, typically solubility in water of less than 10 percent by weight, and water.

In one embodiment, the amount of drift control surfactant present in the end use pesticide concentration is greater than the solubility limit of the drift control surfactant in the end use pesticide composition.

In one embodiment, the end use pesticide composition of the present invention comprises greater than 0.1 wt %, more typically greater than or equal to 0.5 wt % of oleyl alcohol ethoxylated with 5 moles of ethylene oxide per mole of olelyl alcohol as the surfactant drift control agent.

In one embodiment, the end use pesticide composition of the present invention does not comprise more than 0.1 pbw per 100 pbw of the composition not comprise more than 0.01 pbw per 100 pbw of the composition, of any oil, such as a vegetable oil, an alkylated vegetable oil, or a mineral oil and even more typically does not comprise any oil.

In one embodiment, the end use pesticide composition of the present invention does not comprise more than 0.1 pbw per 100 pbw of the composition not comprise more than 0.01 pbw per 100 pbw of the composition, of any polymeric drift control agent, such as a polysaccharide drift control agent, and even more typically does not comprise any polymeric drift control agent.

In one embodiment, the end use pesticide composition of the present invention comprises the surfactant drift control agent as the sole drift control agent of the composition.

In one embodiment, the present invention is directed to a method for controlling spray drift of a spray applied aqueous pesticide composition, comprising: spray applying the end use pesticide composition of present invention to the target pest and/or to the environment of the target pest, wherein the spray applied end use pesticide composition exhibits reduced spray drift compared to an analogous spray applied pesticide composition that lacks the at least one surfactant component of the end use pesticide composition of the present invention.

In one embodiment, the spray applied end use pesticide composition comprising the drift control surfactant component exhibits a droplet size distribution wherein the volume percentage of droplets having a droplet size of less than 150 μm is reduced compared to an analogous pesticide composition that lacks the drift control surfactant, when the compositions are each spray applied under the same condition. In one embodiment, volume percentage of droplets having a droplet size of less than 150 μm in the spray applied pesticide composition comprising the drift control surfactant component at least 5%, or by at least 10 wt %, or by at least 20%, or by at least 25%, smaller than volume percentage of droplets having a droplet size of less than 150 μm in the spray applied pesticide composition lacking the drift control surfactant component, when the compositions are each spray applied through a TeeJet XR8002 flat fan nozzle at a pressure of 40 pounds per square inch ("psi"), wherein the droplet distribution is measured at 30 centimeters below the nozzle tip.

The concentrated pesticide composition of the present invention exhibits good stability and handling properties, including low viscosity, and can be readily diluted with water to form efficacious aqueous end use pesticide compositions that may be spray applied to target pests and/or the environment of the target pests.

Examples 1-12 and Comparative Examples C1-C3

The aqueous spray composition of Comparative Example C1 contained water only. The aqueous spray compositions s of Examples 1-7 were made by mixing specific amounts of surfactant (or their mixture) in water. All of them dispersed in water by slight shaking and turned turbid/milky immediately. The surfactant component in the composition of Example 6 was a 50-50 wt % pre-mixture of sorbitan esters. The description and amount of each surfactant in water for the compositions of Comparative Example C1 and Examples 1-7 are given in TABLE I below.

The compositions of Examples 8-12 and Comparative Examples C2 and C3 each contained pesticides. In those compositions, the surfactant (or their mix) was added in water first and then pesticide composition as listed in the table was added to the composition. The appearance of the composition after addition of pesticide composition remained turbid/milky except for Comparative Examples C2 and C3, where no drift control surfactant was added to the pesticide composition. A 50-50% premix of fatty acid polyethylene glycol ester and sorbitan ester was used to prepare the composition of Ex. 12. The description and relative amount of each of the components in the compositions of Examples 8-12 and Comparative Examples C2 and C3 are given in TABLE II below.

TABLE I

| Non-pesticide Compositions | | |
|---|---|---|
| EX # | Component | Concentration in water (wt %) |
| CEx C1 | Water | 100 |
| Ex 1 | fatty acid polyethylene oxide ester surfactant (Alkamuls VO/2003, Rhodia Inc) | 0.12 |
| Ex 2 | Tridecyl alcohol ethoxylate (Rhodasurf BC420, Rhodia Inc) | 0.12 |
| Ex 3 | Sorbitol polyoxyethylene (20) sorbitan trioleate (Alkamuls PSTO 20, Rhodia Inc) | 0.12 |
| Ex 4 | Polyethylene glycol ester Dioleate (Alkamuls 400DO, Rhodia Inc) | 0.12 |
| Ex 5 | Linear alcohol ethoxylate (Rhodasurf LA3, Rhodia Inc) | 0.12 |
| Ex 6 | Sorbitol monolaurate (Alkamuls SML, Rhodia Inc) | 0.12 |
| Ex 7 | 50-50% wt mix of Sorbitan monooleate (Alkamuls SMO, Rhodia Inc) and polyoxyethylene (20) sorbitan trioleate (Alkamuls PSTO 20, Rhodia Inc) | 0.12 |

TABLE II

| Pesticide Compositions | | | | | | | |
|---|---|---|---|---|---|---|---|
| | EX # | | | | | | |
| Component | CExC2 (wt %) | CExC3 (wt %) | Ex 8 (wt %) | Ex 9 (wt %) | Ex 10 (wt %) | Ex 11 (wt %) | Ex 12 (wt %) |
| Roundup Superconcentrate (Isopropylamine salt of Glyphosate acid, Monsanto) | 2.25 | — | 2.25 | — | — | — | — |
| Roundup Weathermax (Potassium salt of Glyphosate acid, Monsanto) | — | 2.25 | — | 2.25 | 2.25 | 2.25 | 2.25 |
| fatty acid polyethylene oxide ester surfactant (Alkamuls VO/2003, Rhodia Inc) | — | — | 0.5 | — | — | — | 0.06 |
| Tridecyl alcohol ethoxylate (Rhodasurf BC420, Rhodia Inc) | — | — | — | 0.12 | — | — | — |
| Linear alcohol ethoxylate (Rhodasurf LA3, Rhodia Inc) | — | — | — | — | 0.5 | — | — |
| Polyethylene glycol ester Dioleate (Alkamuls 400DO, Rhodia Inc) | — | — | — | — | 0.12 | — | — |
| Sorbitan monooleate (Alkamuls SMO, Rhodia Inc) | — | — | — | — | — | — | 0.06 |
| Water | 97.75 | 97.75 | 97.25 | 97.63 | 97.25 | 97.63 | 97.63 |

Samples of all compositions (Ex. 1-12 and CEx. C1-C3) were sprayed through a TeeJet XR8002 flat fan nozzle at a pressure of 40 psi and the droplet size distribution was measured perpendicular to the plane of spray pattern and 30 cm below the nozzle tip. A Sympatec HELOS VARIO particle size analyzer was used to measure droplets generated in spray compositions using an R6 lens (having a measurement range between 9 and 1750 μm). The results for volume mean diameter ("VMD") and amount of droplets below 150 μm in size (driftable fines, expressed as volume %) for the compositions of Examples 1-12 and Comparative Examples C1-C3 are given in TABLES III and IV below.

TABLE III

| Spray Characteristics of Non-pesticide Compositions | | |
|---|---|---|
| EX# | VMD (μm) | Droplets of size <150 μm (Volume %) |
| CEx C1 | 160 | 53 |
| Ex 1 | 195 | 41 |
| Ex 2 | 196 | 42.5 |
| Ex 3 | 198 | 41 |
| Ex 4 | 205 | 38 |
| Ex 5 | 203 | 36.5 |
| Ex 6 | 193 | 42.8 |
| Ex 7 | 185 | 47 |

TABLE IV

| Spray Characteristics of Pesticide Compositions | | |
|---|---|---|
| EX# | VMD (μm) | Droplets of size <150 μm (Volume %) |
| CEx C2 | 150 | 61 |
| CEx C3 | 150 | 60.5 |
| Ex 8 | 183 | 45 |
| Ex 9 | 168 | 51 |
| Ex 10 | 193 | 39.5 |
| Ex 11 | 165 | 53.4 |
| Ex 12 | 175 | 47.5 |

As seen from the results, each of the compositions of Examples 1-7 exhibit increased VMD and decreased volume of driftable fines compared to the composition of Comparative Example C1, the composition of Example 8 exhibits increased VMD and decreased volume of driftable fines compared to the composition of Comparative Example C2 and each of the compositions of Examples 9-12 exhibit increased VMD and decreased volume of driftable fines compared to the composition of Comparative Example C3.

Examples 13-20 and Comparative Examples C3 and C4

The aqueous spray composition of Comparative Example C3 was made by adding a pesticide composition of Glyphosate potassium salt (Roundup Powermax, Monsanto) in CIPAC water of hardness 340 ppm. The aqueous spray compositions of Examples 13-19 were made as follows: first the drift control surfactant was added to the CIPAC water and then the pesticide composition was added to the mixture. The composition of Comparative Example C4 was made by first adding Ethoxylated Oleyl Alcohol (5 moles of EO) in the CIPAC water and then adding the pesticide composition in the mixture. The description and relative amount of each of the components in the compositions of Examples 13-19 and comparative Example C3 and C4 are shown in TABLE IV.

TABLE V

Composition of Examples 13-19 and Comparative Examples C3 and C4

| Ex. # | Water (wt %) | Glyphosate potassium salt (Roundup Powermax, Monsanto), (wt %) | Drift control surfactant and its amount (wt %) |
|---|---|---|---|
| C. Ex3 | 97.75 | 2.25 | — |
| C. Ex4 | 97.65 | 2.25 | Ethoxylated Oleyl Alcohol (5 moles of EO) 0.1% |
| Ex. 13 | 97.65 | 2.25 | Ethoxylated Tridecyl Alcohol (1 mole of EO) 0.1% |
| Ex. 14 | 97.25 | 2.25 | Ethoxylated Oleyl Alcohol (5 moles of EO) 0.5% |
| Ex. 15 | 97.65 | 2.25 | Alcohol Ethoxylate (Rhodasurf CET2, Rhodia Inc.) 0.1% |
| Ex. 16 | 97.45 | 2.25 | Ethoxylated Tridecyl Alcohol (1 mole of EO) 0.3% |
| Ex. 17 | 97.65 | 2.25 | Alcohol Ethoxylate (Rhodasurf BC-420, Rhodia Inc.) 0.1% |
| Ex. 18 | 97.45 | 2.25 | Alcohol Ethoxylate (Rhodasurf BC-420, Rhodia Inc.) 0.3% |
| Ex. 19 | 97.65 | 2.25 | Sorbitan monooleate (Alkamuls SMO, Rhodia Inc), 0.1% |
| Ex. 20 | 97.45 | 2.25 | Sorbitan monooleate (Alkamuls SMO, Rhodia Inc), 0.3% |

Aqueous spray compositions of Ex. 13-15 and Comparative Examples C3 and C4 were sprayed through a TeeJet AIXR11002 Air Induction nozzle at a pressure of 30 psi and the droplet size distribution was measured perpendicular to the plane of spray pattern and 35 cm below the nozzle tip. Aqueous spray compositions of Examples 16-20 and Comparative Example C3 were sprayed through a TeeJet XR8002 flat fan nozzle at a pressure of 40 psi and the droplet size distribution was measured perpendicular to the plane of spray pattern and 15 cm below the nozzle tip. A Sympatec HELOS VARIO particle size analyzer was used to measure droplets generated in spray compositions using an R7 lens. The results for volume percentage of droplets below 150 μm in size (driftable fines expressed as volume %), volume percentage of droplets between 150 and 500 μm in size (desirable size expressed as volume %), and volume percentage of droplets above 150 μm in size (expressed as volume %) for each composition are given in Table VI below. As shown in TABLE VI below, the compositions of Examples 13-20 each reduced driftable fines below 150 microns and increased the volume of desirable size droplets significantly compared to the composition of Comparative Example C3 and C4.

TABLE VI

Drift performance of Examples 13-15 with AIXR11002 and 16-20 with XR8002 nozzle

| Nozzle | Example # | Droplet of size <150 μm (Volume %) | Droplet of size 150-500 μm (Volume %) | Droplet of size >500 μm (Volume %) |
|---|---|---|---|---|
| AIXR11002; 30 psi | C. Ex. 3 | 22.2 | 70.6 | 7.2 |
| | C. Ex. 4 | 21.9 | 68.9 | 9.2 |
| | Ex. 13 | 9.5 | 72.6 | 17.9 |
| | Ex. 14 | 8.5 | 69.5 | 22.0 |
| | Ex. 15 | 8.7 | 69.6 | 21.7 |
| XR8002; 40 psi | C. Ex. 3 | 48.4 | 50.1 | 1.5 |
| | Ex. 13 | 30.9 | 68.3 | 0.8 |
| | Ex. 16 | 21.4 | 77.4 | 1.2 |
| | Ex. 17 | 43.2 | 55.7 | 1.1 |
| | Ex. 18 | 26.8 | 72.1 | 1.1 |
| | Ex. 19 | 27.6 | 71.2 | 1.2 |
| | Ex. 20 | 29.2 | 69.6 | 1.2 |

Examples 21-23 and Comparative Examples C5 and C6

The compositions of formulation A and B were prepared by blending a drift control surfactant with an aqueous solution of a hydrotrope (Sodium Xylene Sulfonate). The resultant mixture was homogeneous and clear. The amount of components in each composition is set forth in TABLE VII.

TABLE VII

Surfactant Compositions

| Component | Formulation A (wt %) | Formulation B(wt %) |
|---|---|---|
| Drift control surfactant 1 (Alcohol Ethoxylate, Rhodasurf BC-420, Rhodia Inc.) | 10 | — |
| Drift control surfactant 2 (Alcohol Ethoxylate, Rhodasurf CET2, Rhodia Inc.) | — | 10 |
| Hydrotrope solution (40% aqueous solution of Sodium Xylene Sulfonate) | 90 | 90 |
| Stability of formulation at room temperature | Homogeneous, single phase, stable for >24 hours | Homogeneous, single phase, stable for >24 hours |

The aqueous compositions of Examples 21 and 22 were made by diluting compositions A and B in the CIPAC water. The aqueous compositions of Examples 23 were made as follows: first composition B was diluted in the CIPAC water and then a pesticide composition of Glyphosate potassium salt (Roundup Powermax, Monsanto) was added to the mixture. The relative amount of each of the components in the compositions of Examples 21-23 and comparative Example C5 (water only) and C6 (dilution of the pesticide composition in the CIPAC water) are shown in Table VIII. The aqueous spray compositions of Ex. 21-23 and comparative examples C5 and C6 were sprayed through a TeeJet XR8002 flat fan nozzle at a pressure of 40 psi and the droplet size distribution was measured perpendicular to the plane of spray pattern and 30 cm below the nozzle tip. A Sympatec HELOS VARIO particle size analyzer was used to measure droplets generated in spray compositions using an R7 lens. The results for volume percentage of droplets below 150 μm in size (driftable fines, expressed as volume %), volume percentage of droplets between 150 and 500 μm in size (desirable size expressed as volume %), and volume percentage of droplets above 150 μm in size (expressed as volume %) for each composition are given in TABLE VIII below. As seen from the table VIII, the compositions of Examples 21-23 each reduced driftable fines below 150 microns and increased the volume of desirable size droplets compared to the composition of Comparative Example C5 and C6 lacking the drift control surfactant.

TABLE VIII

Drift performance of Examples 21-23 and Comparative Examples C5 and C6

| Example # | Composition | Droplet of size <150 μm (Volume %) | Droplet of size 150-500 μm (Volume %) | Droplet of size >500 μm (Volume %) |
|---|---|---|---|---|
| C. Ex. 5 | Water only | 53.7 | 45.7 | 0.6 |
| C. Ex. 6 | 2.25 wt % Glyphosate potassium salt (Roundup Powermax) in water | 57.4 | 41.8 | 0.8 |
| Ex. 21 | 2 wt % A in water | 38.8 | 60.4 | 0.9 |
| Ex. 22 | 2 wt % A in water | 43.5 | 55.5 | 1.0 |
| Ex. 23 | 2 wt % B + 2.25 wt % Glyphosate potassium salt (Roundup Powermax) in water | 51.9 | 47.6 | 0.5 |

Examples 24 and 25 and Comparative Examples C7 and C8

The aqueous spray composition of Comparative Example 7 was water only. The aqueous spray compositions of Examples 24 and 25 and Comparative Example C8 were made mixing a respective surfactant with water. The description of the components of the compositions and the amounts used outlined in TABLE IX below.

Aqueous spray compositions of Examples 24-25 and Comparative Example C7 and C8 were sprayed through a TeeJet XR8002 flat fan nozzle at a pressure of 40 psi and the droplet size distribution was measured perpendicular to the plane of spray pattern and 15 cm below the nozzle tip. A Sympatec HELOS VARIO particle size analyzer was used to measure droplets generated in spray compositions using an R7 lens. The results for volume percentage of droplets below 150 μm in size (driftable fines expressed as volume %), for each composition is given in TABLE IX below. As shown in TABLE IX below, the compositions of Examples 24-25 each reduced the amount of driftable fine droplets below 150 microns in size compared to the composition of Comparative Examples C7 and C8 and the composition of Example C8, which contained a surfactant having a solubility of greater than 10 wt %, exhibited a significant increase in the amount of undesirable small spray droplets compared to the composition of Comparative Example C7, which contained water alone.

TABLE IX

Composition and Drift Performance of Examples 24-25 and Comparative Examples C7 and C8

| EX # | Components | Amount of Surfactant Component (wt % in water) | Solubility of surfactant component in water | Appearance of composition | Droplets <150 microns (vol %) |
|---|---|---|---|---|---|
| C. EX. C7 | Water | 0 | — | clear | 43.5 |
| EX. 24 | Ethoxylated (3 EO) tridecyl alcohol | 0.3% | not soluble | turbid dispersion | 22.1 |
| EX. 25 | Ethoxylated (6 EO) tridecyl alcohol | 0.3% | not soluble | turbid dispersion | 22.5 |
| C. EX. C8 | Ethoxylated (9 EO) tridecyl alcohol | 0.3% | Solubility >10% | clear solution | 58.5 |

The invention claimed is:

1. A method for controlling spray drift of an aqueous end use pesticide composition, comprising:

incorporating in the aqueous end use pesticide composition comprising a pesticide, in an amount effective as a drift control agent, an aqueous surfactant composition, said surfactant composition comprising (i) water, at least 10 percent by weight of at least one surfactant having a solubility in water of less than 10 percent by weight, wherein the surfactant is selected from alkoxylated alcohol surfactants and alkoxylated sorbitan esters, and (ii) at least one hydrotrope selected from alkaryl sulfonate salts, wherein the hydrotrope is present in an amount effective to solubilize the at least one surfactant in the surfactant composition so that the water, surfactant, and hydrotrope form a homogeneous single phase solution at 25° C.; and spray applying the aqueous end use pesticide composition to a target pest and/or to the environment of the target pest, wherein the spray applied aqueous end use pesticide composition exhibits improved drift control compared to an analogous spray applied aqueous end use pesticide composition that lacks the at least one surfactant, and wherein the alkaryl sulfonate salt is selected from sodium xylene sulfonate or sodium toluene sulfonate.

2. A method for controlling spray drift of an aqueous end use pesticide composition, comprising:

incorporating in the aqueous end use pesticide composition comprising a pesticide, in an amount effective as a drift control agent, an aqueous surfactant composition, said surfactant composition comprising (i) water, at least 10 percent by weight of at least one surfactant having a solubility in water of less than 10 percent by weight, wherein the surfactant is selected from alkoxylated alcohol surfactants and alkoxylated sorbitan esters, and (ii) at least one hydrotrope selected from alkaryl sulfonate salts, wherein the hydrotrope is present in an amount effective to solubilize the at least one surfactant in the surfactant composition so that the water, surfactant, and hydrotrope form a homogeneous single phase solution at 25° C.; and spray applying the aqueous end use pesticide composition to a target pest and/or to the environment of the target pest, wherein the spray applied aqueous end use pesticide composition exhibits improved drift control compared to an analogous spray applied aqueous end use pesticide composition that lacks the at least one surfactant, and wherein the alkaryl sulfonate salt is sodium xylene sulfonate.

* * * * *